(12) United States Patent
Mattsson

(10) Patent No.: US 7,129,927 B2
(45) Date of Patent: Oct. 31, 2006

(54) GESTURE RECOGNITION SYSTEM

(75) Inventor: Hans Mattsson, Gothenburg (SE)

(73) Assignee: Hans Arvid Mattson, Lund (SE)

( * ) Notice: Subject to any disclaimer, the term of this patent is extended or adjusted under 35 U.S.C. 154(b) by 66 days.

(21) Appl. No.: 10/242,631

(22) Filed: Sep. 13, 2002

(65) Prior Publication Data
US 2003/0076293 A1    Apr. 24, 2003

Related U.S. Application Data

(63) Continuation of application No. PCT/SE01/00528, filed on Mar. 13, 2001.

(30) Foreign Application Priority Data
Mar. 13, 2000    (SE) .................................... 0000850

(51) Int. Cl.
*G09G 5/08*   (2006.01)
(52) U.S. Cl. ...................... 345/158; 345/863; 715/863
(58) Field of Classification Search ................ 345/158,
345/790, 700, 863; 348/14.01, 14.08; 715/790,
715/863; *G06K 11/08*
See application file for complete search history.

(56) References Cited

U.S. PATENT DOCUMENTS

| | | | | |
|---|---|---|---|---|
| 4,843,568 A | * | 6/1989 | Krueger et al. ............. 382/100 |
| 5,025,314 A | * | 6/1991 | Tang et al. ............... 348/14.08 |
| 5,239,373 A | * | 8/1993 | Tang et al. ............... 348/14.01 |
| 5,581,276 A | * | 12/1996 | Cipolla et al. ............... 345/156 |
| 5,594,469 A |  | 1/1997 | Freeman et al. |
| 5,616,078 A |  | 4/1997 | Oh |
| 5,617,312 A |  | 4/1997 | Iura et al. |
| 5,877,778 A | * | 3/1999 | Dow et al. .................. 345/474 |
| 5,880,725 A | * | 3/1999 | Southgate ................... 345/790 |
| 5,982,352 A | * | 11/1999 | Pryor ......................... 345/156 |
| 6,072,494 A | * | 6/2000 | Nguyen ...................... 715/863 |
| 6,154,723 A | * | 11/2000 | Cox et al. ................... 704/270 |
| 6,335,977 B1 | * | 1/2002 | Kage .......................... 382/107 |

FOREIGN PATENT DOCUMENTS

| | | |
|---|---|---|
| DE | 196 32 273 | 2/1998 |
| EP | 0 905 644 A2 | 3/1999 |
| WO | 99/64961 | 12/1999 |

OTHER PUBLICATIONS

Kuno et al., "Vision-Based Human Interface with User-Centered Frame", Proceedings of the IEEE/RSJ/GI International Conference in Munich, Germany, vol. 3, pp. 2023-2029, Sep. 1994, XP510665.

* cited by examiner

*Primary Examiner*—Richard Hjerpe
*Assistant Examiner*—Kimnhung Nguyen
(74) *Attorney, Agent, or Firm*—Young & Thompson

(57) ABSTRACT

A gesture recognition system includes: elements for detecting and generating a signal corresponding a number of markers arranged on an object, elements for processing the signal from the detecting elements, members for detecting position of the markers in the signal. The markers are divided into first and second set of markers, the first set of markers constituting a reference position and the system comprises elements for detecting movement of the second set of markers and generating a signal as a valid movement with respect to the reference position.

19 Claims, 4 Drawing Sheets

- — Control commands
- ⋯⋯ Gstures
- —·— GUI data
- —··— Stream of makers
- — — — Commands to externa devices

GESTURE RECOGNITION SYSTEM

FIELD OF THE INVENTION

The present invention relates to a gesture recognition system comprising: means for detecting and generating a signal corresponding a number of markers arranged on a body or part of body of a person, means for processing said signal from said detecting means, means for detecting position of said markers in said signal.

BACKGROUND OF THE INVENTION

The rapid development of the motion analyses systems and computer-controlled devices has introduced possibility of new ways of interacting with computers. One preferred method is to use different body parts as a commanding device, i.e. using movements to enter commands into the operating system of the computer or control peripheral devices.

However, the known methods and systems are rather complex and usually analyse the entire body or a large area.

In WO 99/34276, a system and method for constructing three-dimensional images using camera-based gesture inputs of a system user is described. The system comprises a computer-readable memory, a video camera for generating video signals indicative of the gestures of the system user and an interaction area surrounding the system user, and a video image display. The video image display is positioned in front of the system users. The system further comprises a microprocessor for processing the video signals, in accordance with a program stored in the computer-readable memory, to determine the three-dimensional positions of the body and principle body parts of the system user. The microprocessor constructs three-dimensional images of the system user and interaction area on the video image display based upon the three-dimensional positions of the body and principle body parts of the system user. The video image display shows three-dimensional graphical objects superimposed to appear as if they occupy the interaction area, and movement by the system user causes apparent movement of the superimposed, three-dimensional objects displayed on the video image display.

According to U.S. Pat. No. 6,002,808, a system is provided for rapidly recognizing hand gestures for the control of computer graphics, in which image moment calculations are utilized to determine an overall equivalent rectangle corresponding to hand position, orientation and size, with size in one embodiment correlating to the width of the hand. In a further embodiment, a hole generated through the utilization of the touching of the forefinger with the thumb provides a special trigger gesture recognized through the corresponding hole in the binary representation of the hand. In a further embodiment, image moments of images of other objects are detected for controlling or directing onscreen images.

A method and an apparatus are described in U.S. Pat. No. 5,576,727 for use with a computer for providing commands to a computer through tracked manual gestures and for providing feedback to the user through forces applied to the interface. A user manipulatable object is coupled to a mechanical linkage, which is, in turn, supportable on a fixed surface. The mechanical linkage or the user manipulatable object is tracked by sensors for sensing the location and/or orientation of the object. A multi-processor system architecture is disclosed wherein a host computer system is interfaced with a dedicated microprocessor which is responsive to the output of the sensors and provides the host computer with information derived from the sensors. The host computer has an application program, which responds to the information provided via the microprocessor and which can provide force-feedback commands back to the microprocessor. The force feedback is felt by a user via the user manipulatable object.

SUMMARY OF THE INVENTION

Thus, the main object of the present invention is to provide a gesture recognition method and system, which allow real time gesture recognition without a need for complex computing resources.

Therefore, in the initially mentioned system, the markers are divided into first and second set of markers, said first set of markers constituting a reference position and that said system comprises means for detecting movement of said second set of markers and generating a signal as a valid movement with respect to said reference position.

BRIEF DESCRIPTION OF THE DRAWING

In the following, the invention will be further described in a non-limiting way with reference to the accompanying drawings, in which.

DETAILED DESCRIPTION OF THE INVENTION

Figure 1:
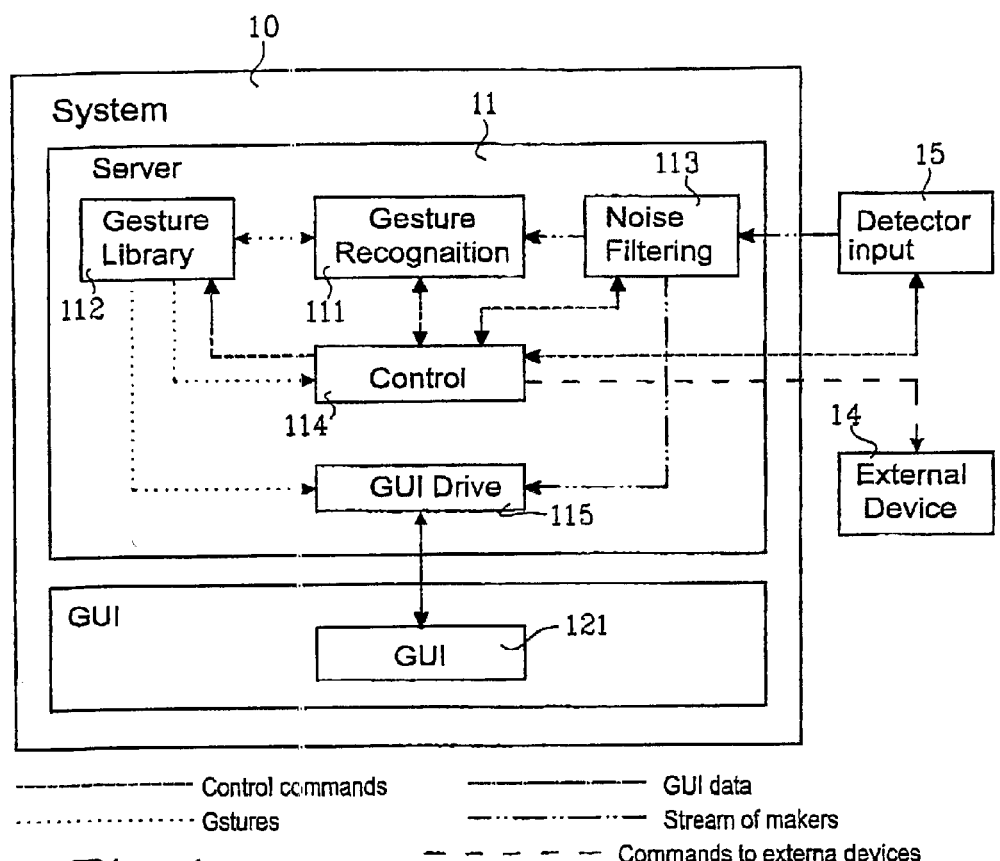
FIG. 1 is a block diagram illustrating the main parts of the system according to the invention.

The system 10 according to the invention comprises two main parts, a Server part 11 and GUI part 12. The server part 11 comprises a number of modules: Gesture Recognition 111, Gesture Library 112, Noise Filtering 113, Control 114 and GUI Drive 115. The GUI part 12 comprises GUI module 121. Moreover, the system interfaces a Camera input 13 and external drivers 14.

Following is description of the various modules:

Gesture Recognition 111

This module takes an input stream of marker positions, assuming it traces the gesture to be recognized. This gesture is called a "research gesture". The main task of the module is to compare a research gesture to template gestures and to produce an estimation of similarity for every gesture in a library.

Since the module provides low-level routines to accomplish the task of gesture recognition and it is designed to be fully controllable by the "Control Module" there is no application-specific code here.

The research gesture is provided inside the module from the input stream of markers, coming from "Noise Filtering"

module. The "Control" module, which registers a callback function from "Gesture Recognition" to inform the "Noise Filtering" where to send the stream of markers to.

In the other hand "Gesture Recognition" module is populated by a large set of template gestures, coming from "Gesture Library". Once a research gesture is committed by the "Control" module to be stored in a "Gesture Library", the "Gesture Library" grabs the data from "Gesture Recognition" for storing in a database.

The recognition process can be divided into the following steps: Gesture fragmentation: In order to fragment the gesture, crucial points are looked for. These are points, e.g. where gestures make a sharp turn, change directions and so on. These crucial points form a skeleton of a gesture.

Coordinate transformations: Every gesture can be entered in various places in space, under various angles, and may be scaled as well. Thus, the gesture must be transformed to some normalized coordinate system. Preferably, but not exclusively, 4×4 transformation matrices are used to accomplish this goal.

An average value of similarity for skeletons is thus calculated. This value is the average distance between corresponding crucial points normalized by the length of the skeleton (the length of the gesture). This is the most important criterion of similarity for gestures.

The next step is to compare gesture fragments. The fragments also have to be normalized so that start and end point of the comparing fragments can be located in the same position in the coordinate system. The algorithm of fragment comparison is similar to the calculation of the area between two fragments. The lower the value of area (normalized by the length of the fragment) is, the more resemblance is obtained.

The last step is to combine the results of step 3 and results of step 4 for every fragment.

Gesture Library 112

The Gesture library module reads template gestures from a memory and populates the module "Gesture Recognition" with them. The library provides all functionality needed in order to handle a database of gestures. Moreover, the gestures have additional attributes, describing which user they belong to, what command (or a sequence of commands) they are attached to and in what modes they are operational in.

This module interacts mostly with the "Gesture Recognition" module in order to populate it with a number of gestures from the database and the "Gesture Recognition" may also provide it with data for a new gesture committed to be saved into the database.

In other hand, most attributes of the gestures are intended to be interpreted by the "Control" module. Thus, the "Control" module has access to read, modify and remove any properties of the gestures.

One very specific use of the module is to provide the "GUI Driver" module with information about the appearance of the gesture. This is necessary to be able to illustrate the gesture on a display.

The main requirement for this module is to be able to serve needs of various "Control" modules. In order to accomplish this goal, every gesture in addition to data, required by the "Gesture Recognition" module, may keep any number of key=value pairs. These slots are intended to be used in the "Control" system. Typical use of such slots include:
  name of the gesture,
  which user the gesture belong to,
  which mode the gesture is operational in, and
  which command(s) to the external device the gesture is bound to.

Noise Filtering 113

The main function of this module is to reduce the noise in marker data so that the "Gesture Recognition" will recognize the gestures without being confused by any high-frequency oscillation of the marker.

A so called median filter can be used, which means that the filtered output for a marker at time $t_1$ will be taken from the middle of a sorted array generated from the positions of markers in a range of times from $t_{1-n}$ to $t_{1+n}$.

The common problem with any kind of filters is a delay introduced by the filter between a signal before and a signal after the filter. In a case of median filter the delay is n times. Using a camera providing a sample rate of for example 100 Hz and assuming n=2, a delay of 20 ms is obtained. The camera can be both for visible light and/or Infrared (IR) light.

Control 114

The tasks of this module are:
  system startup and initialization of all modules,
  user login and logout,
  switching modes,
  macro expansion,
  issuing commands to the external device,
  user customization.

The "Control" module controls all modules with exception for the "GUI" module, which can be operated by "GUI Driver".

The Control module uses data stored in the "Gesture Library" for tasks such as:
  controlling the "External Device"
  switching modes
  operating the user interface and so on GUI Driver 115

This module serves as an intermediate level between the Control and the GUI modules. This module prepares the data for "GUI" to be displayed without complex conversions, accepts the user commands and passes them back to the Control module.

There are some specific routines, e.g.:
Mouse emulation using "Camera Input" module.
Aids the "GUI" module preparing most data for displaying the gesture on the screen under various 3-dimensional transformation, possibly in animated way and transforming coordinate system on the fly.
Keyboard emulation to allow user to enter the text data by "typing in the air".

There are two very specific uses of this module:

The first is to prepare data for mouse emulation using "Camera Input" module. In order to be able to accomplish this task, the stream of marker positions are directly sent to the "GUI Driver" module.

The second is the ability to draw the gesture on the user's screen. In order to accomplish this task gesture's data is accessed.

GUI (Graphic User Interface) 121

This module drives the entire user interface and interacts with the rest of the system through "GUI Driver" module.

Detector Input 13

The Detector Input (camera input in case of cameras are used) refers to a system with few cameras located in various places in a working space being directed under different angles. The output from the cameras is sent to a system, which detects location of markers and traces this location from one frame to another. Preferably, there are stream of 2-dimensional coordinates from every camera, which are combined together, forming a single stream of 3-dimensional coordinates for every registered marker. These are the data system receives as input.

There are special requirements on this module, including:
Reliability; it is very likely, that the markers can be lost by tracing algorithms, because they may be covered by some objects in space so that they will not be seen from the cameras. This may require some extrapolation using the tendency of marker movements right before the marker was lost and information from the cameras, which still trace the marker may help to perform this extrapolation task.
Noise filtering; the influence of noise filtering is described in section below. Arranging the noise filtering inside the "Camera Input" module simplifies the task of recovering lost markers, because additional delays and ability "to foresee" are obtained. The marker may get into the view filed of the camera again and the task of extrapolation turns into the task of interpolation for just few lost moments.

External Device 14

The "External Device" refers to external systems, that the system of the invention is intended to control. One of the most important features of system is relative independency from the "External Device".

The control of the external devices, protocols of data exchange etc., is assumed to be known to a skilled person not described further herein.

However, the system is adaptable to any external devices, which can be controlled by a set, e.g. of Boolean signals (ON/OFF) and some commands may have an arbitrary floating-point argument (it can have meaning of speed, altitude and so on).

The gesture recognition is carried out by positioning a number of markers on a human body or using parts of the body as markers.

Figure 2:
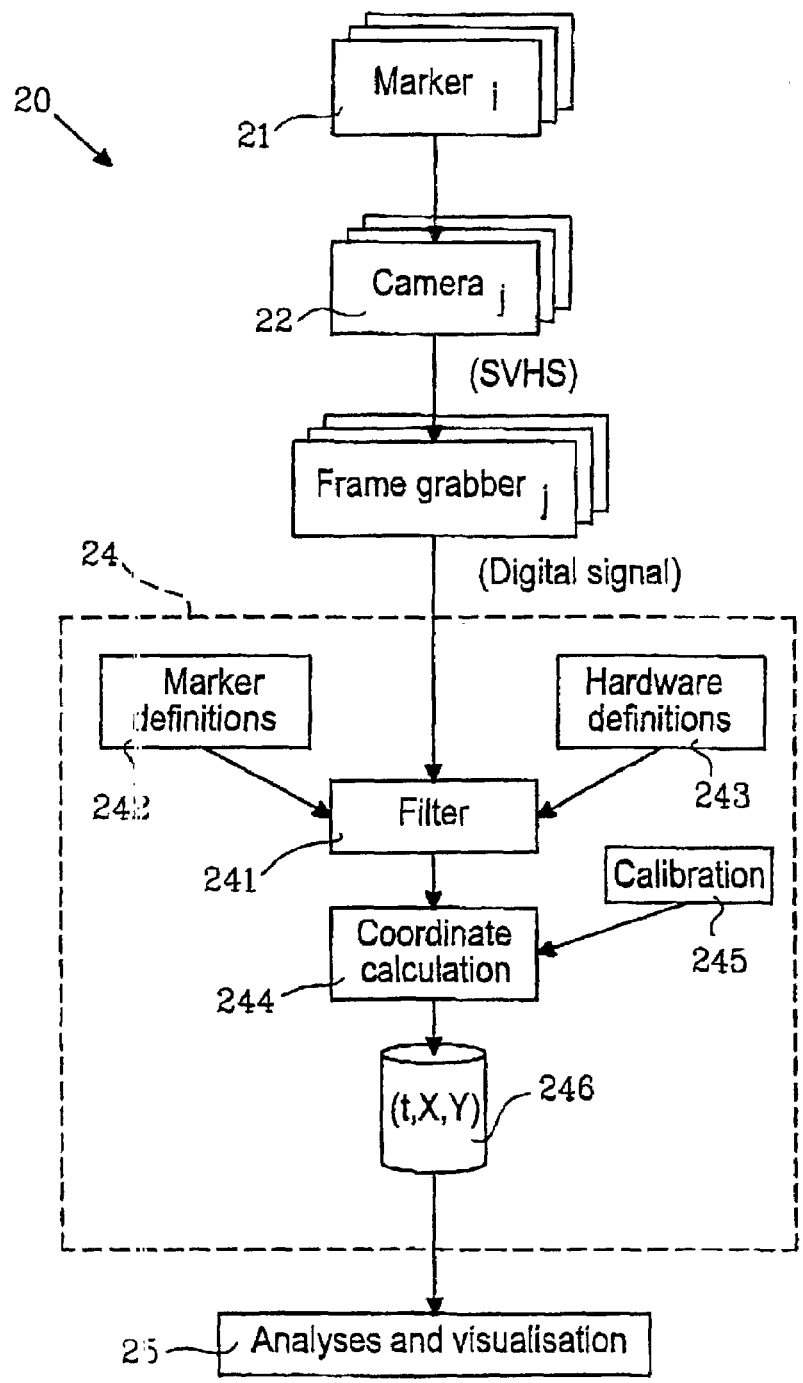
FIG. 2 is a block diagram illustrating the main parts of the marker tracking system according to the invention.

In the server 11 here denoted system 20 of recognition is described with reference to FIG. 2. The main task of the module is to work as a tracking system and to filter digitised information from each optical detection device (camera) and calculate 3D coordinates for markers.

Tracking module consists of the following main components:
Optical detection devices (cameras) 22,
Frame grabbers 23,
Set of (colour) markers 21,
A control system 24.

Preferably, the markers (i=1 to m) are passive objects, which can be coloured. However, active markers can also be used. Each marker has its own unique colour (e.g. RGB combination).

Marker's 21 positions are recorded by optical detection devices 22, such as cameras. The number of cameras: j=1 to n (where n>=1).

Preferably, SVHS video signals from optical detection devices are used and digitised by the frame grabbers 23. The frame grabber stores bitmap images from each optical detection device under each time frame. The process is synchronised.

The control system 24 comprises a filtering module 241, a marker definition module 242, a hardware definition module 243, a 3D coordinate calculator 244, calibration module 245 and a database 246. The system filters the stored bitmap image data received from frame grabbers 23 and prepares coordinates (X, Y) for all markers from all cameras in a time frame t. It means that in each moment of time $t_1$ the following data will be available from each optical detection device:

| Marker Number | Moment of Time | X | Y |
|---|---|---|---|
| Camera 1 | | | |
| 1 | $t_1$ | $X_{11}$ | $Y_{11}$ |
| 2 | $t_1$ | $X_{21}$ | $Y_{21}$ |
| 3 | $t_1$ | $X_{31}$ | $Y_{31}$ |
| 4 | $t_1$ | $X_{41}$ | $Y_{41}$ |
| ... | $t_1$ | ... | ... |
| Camera 2 | | | |
| 1 | $t_1$ | $X_{12}$ | $Y_{12}$ |
| 2 | $t_1$ | $X_{22}$ | $Y_{22}$ |
| 3 | $t_1$ | $X_{32}$ | $Y_{32}$ |
| 4 | $t_1$ | $X_{42}$ | $Y_{42}$ |
| ... | $t_1$ | ... | ... |

Based on the information received from the filter module 241, six (DOF: Degree Of Freedom) coordinates for markers are calculated by 3D coordinate calculation module 244.

| Marker Number | Moment of Time | X | Y | Z |
|---|---|---|---|---|
| 1 | $t_1$ | $X_1$ | $Y_1$ | $Z_1$ |
| 2 | $t_1$ | $X_2$ | $Y_2$ | $Z_2$ |
| 3 | $t_1$ | $X_3$ | $Y_3$ | $Z_3$ |
| 4 | $t_1$ | $X_4$ | $Y_4$ | $Z_4$ |
| ... | $t_1$ | ... | ... | ... |

The system uses the calibration module 246 to define a zero point in space for 3D coordinate calculation.

Marker definition module 242 contains description of currently used markers. It should include a possibility to define multicolour markers too.

Hardware definition module includes settings for optical detection devices, frame grabbers etc.

It has the following set of tasks:
To read and filter the digitised signal from all cameras (received from frame grabbers)—based on the information about the corresponding colour combination for each marker extract coordinate packages (t, X, Y) for each marker (i=1 to m) from each camera (j=1 to n)
Calibration of optical detection devices
To define markers (shape, size, colour combination, etc.)
Transform this data to co-ordinate packages (t, X, Y, Z) for each marker (i=1 to m) in each moment of time, using the information of cameras calibration
To save the set of colour combinations for system markers
Provide a user with a possibility to define hardware settings
Provide the user with responses (warnings, messages etc.)
The systems can use colored markers to keep track of the user and to serve for user gesture commands presentation.

Figure 3:
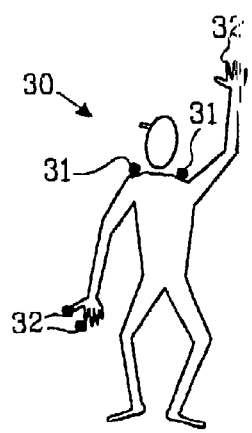
FIG. 3 shows schematically marker arrangements on a body of a person.

For example, two sets of markers will always be available in the system: Alfa and Beta markers, see FIG. 3.

The Alfa markers 31 help the system to keep track the user 30. As the Alfa markers are worn on the shoulders of the user a horizontal line or plane could be calculated. This line/plane will indicate the lowest border of the user command area. To command the system, the user will have to raise hands above this line.

Beta markers 32 serve for the user gesture commands presentation.

The number of markers depends on the application and tasks. For example there are two or more Alfa and three or more Beta markers in the system. For Virtual Reality applications, the number of Beta markers can be increased.

In general, the markers are small, ID-specific, sequential color patterns. The single color fields of the patterns shall be large enough to be discovered by the cameras (within a reasonable distance) and small enough to enable the system to calculate shifts in small movements of the user.

Figure 4:
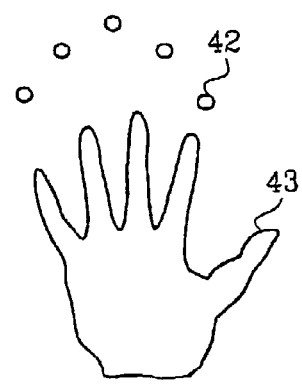
FIG. 4 is a schematic view of a hand glove used as markers.

The most functional way of Beta markers presentation for the VR applications is to make gloves with color markers printed on their fingertips, see FIGS. 4a and 4b, which illustrate a glove representation 43 from the back of the hand and corresponding marker representations 42 generated as fingertips. It is possible to paint the body part as markers.

Each glove can have two base colors: for back and for palm of the hand. Every fingertip can be marked with its own unique color combination.

For applications, which do not need such detailed information about the hand gestures, only two fingertips (thumb and index finger) could be used.

To distinguish between the hands, the gloves have different base colors for right and left hands. For one hand the pair of original (for the palm of the hand) and inverted color (for the back of the hand) could be used.

There are several ways of printing markers on the fingertips: the basic color of the glove is solid while the color of the fingertip acting as marker can be stripes or barcode, and the combination of the base color of the glove and the fingertip color identify the marker of the finger uniquely.

Both methods allow using only one color per finger to get four different markers for two fingers and twenty color combinations for ten fingers, using only five colors.

The first markers interpretation way has a more complicated variation, the barcode view for markers. This technique gives a possibility to have the additional parameter for marker definition, the setting of the corresponding code.

Barcode like and striped variants of markers presentation are useful only for high-resolution cameras. In this case there are more exacting requirements of distance restrictions too.

For standard camera configuration the second variant of markers presentation is acceptable.

Markers definition module should supply the user of the system with the possibility to define currently used color markers.

The following information about currently used markers should be possible to define:
The Marker types (Alfa, Beta). For each marker type the following data should be described:
Marker shape (circle, square, etc.)
Marker colour combination includes:
The description of color combination for Beta markers, situated on fingers is defined as following:
The definition of base colors for gloves: right and left hands (back and palm of each hand). The color of the back of the hand is the inverted color of the palm of the hand
The definition for color of each fingertip of the hand (so, using only 5 additional colors, 20 pseudo multicolor Beta markers, situated on the user fingertips are obtained).
The description of color combination for possible remaining Beta markers and Alfa markers.

Color properties definition.

It is very important to choose the combination of adjacent colors in a way to prohibit mistakes in the recognition process.

The combination of base color of glove and a color of the fingertip gives a possibility to define pseudo multicolor markers on the hand fingers. The system allows possibility to define multicolor, striped and barcode markers (in case of high resolution cameras using).

The effects of marker material, interior lighting and shadows to the detection of markers should be minimized. In the 'Color properties definition' section a logical scheme of "distances" between colors can be established.

The 'Marker Recognition Module' (further called MRM module) should recognize (t,X,Y) packages for all markers from all cameras in each moment of time t based on the information from 'Markers Definition Module' (MDM) and digitised data received from optical detection devices.

The two types of markers recognition are realized:
Beta markers recognition (recognition of the center of the of the fingertip color shape, taking into account the base color of the glove, i.e. the center of color spot rounded by base color of the glove)
Alfa and remaining Beta markers (if exist) recognition (recognition the center of the solid color markers, situated outside the gloves)

Requirements for the Markers Recognition Module (MRM):
The module is designed in a way to make possible to add possibilities to recognize future multicolor, striped and barcode markers (in case of high resolution cameras using)
Reliability
Speed of recognition
Scalability. The MRM module should scalable to have a possibility to be easily used in other applications.
Compatibility. The development tool should allow working with different computer platforms. The MRM module should be compatible for working with different types of frame grabbers.

To be able to position the markers, methods are used transform the positions into two or three-dimensional coordinates.

The task of solving transformation matrix requires the definition how four points should be transformed in space. All these four points should not lie on a single plane. In fact for the sake of precision the best choice would be to have four points, so that they form tetrahedron will all vertices with the same length.

However, if there are only two points, a third one must be found first. In the following a method is described for finding a third point by two given points, so that three points will form a triangle in space with all sides being equal.

Assuming that there are three points $P_1$, $P_2$ and $P_3$ each defined as $P_1(x_1, y_1, z_1)$, $P_2(x_2, y_2, z_2)$ and $P_3(X_3, y_3, z_3)$ then a fourth point $P_4(x_4, y_4, z_4)$, so that a triangle $P_1 P_2 P_4$ having equal sides with all four points in one plane is sought.

The general equation for a plane is the following:

$$Ax+By+Cz+D=0 \qquad (1)$$

Another important formula is:

$$x \cos \alpha_x + y \cos \alpha_y + z \cos \alpha_z - p = 0 \qquad (2)$$

Note, that $\alpha_x$, $\cos \alpha_y$ and $\cos \alpha_z$ define cosiness for a vector perpendicular to the plane.

Also, three points can define the plane:

$$\begin{vmatrix} x & y & z & 1 \\ x_1 & y_1 & z_1 & 1 \\ x_2 & y_2 & z_2 & 1 \\ x_3 & y_3 & z_3 & 1 \end{vmatrix} = 0 \qquad (3)$$

Moreover, $$\begin{cases} L = \sqrt{A^2 + B^2 + C^2} \\ \cos\alpha_x = A/L \\ \cos\alpha_y = B/L \\ \cos\alpha_z = C/L \end{cases} \qquad (4)$$

Wherein $$\begin{cases} A = \begin{vmatrix} y_1 & z_1 & 1 \\ y_2 & z_2 & 1 \\ y_3 & z_3 & 1 \end{vmatrix} = 0 \\ B = \begin{vmatrix} z_1 & x_1 & 1 \\ z_2 & x_2 & 1 \\ z_3 & x_3 & 1 \end{vmatrix} = 0 \\ A = \begin{vmatrix} x_1 & y_1 & 1 \\ x_2 & y_2 & 1 \\ x_3 & y_3 & 1 \end{vmatrix} = 0 \end{cases} \qquad (5)$$

which in combination with formula 4 and normal matrix calculation gives A, B, C, $\cos\alpha_x$, $\cos\alpha_y$ and $\cos\alpha_z$, and finally a vector can be built forming the middle of the triangle $P_1P_2P_3$ to the point $P_4$.

For finding a point p on a line ab so that |pc|=min, where c is an arbitrary point in space and a and b are distinct points, a perpendicular to the line ab from point c is found. A point where this perpendicular crosses the line ab is a point we are looking for.

Having three points $a(a_x, a_y, a_z)$, $b(b_x, b_y, b_z)$, $c(c_x, c_y, c_z)$ and point $p(x, y, z)$, so that line ab is perpendicular to pc and point p lies on the line ab.

From vector algebra, it is known that vector product for perpendicular vectors is 0:

$$a \cdot b = |a||b| \cos\gamma \qquad (6)$$

Expressed in Cartesian coordinates for 3d coordinate system it appears to be:

$$a \cdot b = a_x b_x + a_y b_y + a_z b_z \qquad (7)$$

The line equation in Cartesian coordinates, assuming that two distinct points are $p_1(x_1, y_1, z_1)$ and $p_2(x_2, y_2, z_2)$, a line is defined:

$$\frac{x - x_1}{x_2 - x_1} = \frac{y - y_1}{y_2 - y_1} = \frac{z - z_1}{z_2 - z_1} \qquad (8)$$

Thus, the system of three equations for three variables are obtained:

$$\begin{cases} \vec{ab} \cdot \vec{pc} = 0 \\ \dfrac{y - a_y}{b_y - a_y} = \dfrac{x - a_x}{b_x - a_x} \\ \dfrac{z - a_z}{b_z - a_z} = \dfrac{x - a_x}{b_x - a_x} \end{cases} \qquad (9)$$

Assuming vector $v(v_x, v_y, v_z) = \vec{ab} = v(bx-ax, by-ay, bz-az)$
Then the following parameters for p are obtained:

$$v_x = b_x - a_x \qquad (10)$$
$$v_y = b_y - a_y$$
$$v_z = b_z - a_z$$

$$x = \frac{v_x(c_x v_x + c_y v_y + c_z v_z - a_y v_y - a_z v_z) + a_x(v_y^2 + v_z^2)}{v_x^2 + v_y^2 + v_z^2}$$

$$y = (x - a_x)\frac{v_y}{v_x} + a_y$$

$$z = (x - a_x)\frac{v_z}{v_x} + a_z$$

$$v_x^2 + v_y^2 + v_z^2 = l_2,$$

where l is the distance between the points a and b.

The task of solving transformation matrix requires the definition how four points should be transformed in space. All these four points should not lie on a single plane. In fact for the sake of precision the best choice would be to have four points, so that they form tetrahedron will all vertices with the same length.

In this particular case we know only how two points should be translated and we also know one more point. However, third point in a source and destination coordinate system is not identical, and this third point can be used only to define a plane, where real third point can be located.

Thus, if there are two points $P_1(a_x, a_y, a_z)$ and $P_2(b_x, b_y, b_z)$ a third point $P_3(c_x, c_y, c_z)$ is sought so that a triangle $P_1P_2P_3$ with equal sides is obtained.

If $P_1$ and $P_2$ build a vector $\vec{P_1P_2}$, following is valid:

$$\begin{cases} \cos\alpha_x = \dfrac{x_2 - x_1}{\sqrt{(x_2-x_1)^2 + (y_2-y_1)^2 + (z_2-z_1)^2}} \\ \cos\alpha_y = \dfrac{y_2 - y_1}{\sqrt{(x_2-x_1)^2 + (y_2-y_1)^2 + (z_2-z_1)^2}} \\ \cos\alpha_z = \dfrac{z_2 - z_1}{\sqrt{(x_2-x_1)^2 + (y_2-y_1)^2 + (z_2-z_1)^2}} \\ \cos^2\alpha_x + \cos^2\alpha_y + \cos^2\alpha_z = 1 \end{cases} \qquad (11)$$

$$\begin{cases} \cos\alpha_x \cos\alpha'_x + \cos\alpha_y \cos\alpha'_x + \cos\alpha_z \cos\alpha'_x = \cos 60 \\ \cos^2\alpha'_x + \cos^2\alpha'_y + \cos^2\alpha'_z = \cos 90 \end{cases} \qquad (12)$$

which for $\cos 90 = 1$ and $\cos 60 = 0.5$ gives

-continued $$\begin{cases} 2\cos\alpha_x \cos\alpha'_x + 2\cos\alpha_y \cos\alpha'_x + 2\cos\alpha_z \cos\alpha'_x = 1 \\ \cos^2\alpha'_x + \cos^2\alpha'_y + \cos^2\alpha'_z = 1 \end{cases} \quad (13)$$

and for $$\begin{cases} k_1 = 2\cos\alpha_x \\ k_2 = 2\cos\alpha_y \\ K_3 = 2\cos\alpha_z \\ x_1 = \cos\alpha'_x \\ x_2 = \cos\alpha'_x \\ x_3 = \cos\alpha'_x \end{cases} \quad (14)$$

and assuming that $x_3$ equals 0, the solution is $$(k_j^2 + k_i^2)x_j^2 - 2k_j^2 x_j + 1 - k_i^2 = 0 \quad (15)$$

$$D = 4k_j^2 + 4(k_i^2 + k_j^2)(1 - k_i^2) \quad (16)$$

which gives $$x_j = \frac{2k_j \pm \sqrt{D}}{2(k_j^2 + k_i^2)} \quad (17)$$

For transformation of given set of four points $P_1(x_1, y_1, z_1)$, $P_2(x_2, y_2, z_2)$, $P_3(x_3, y_3, z_3)$ and $P_4(x_4, y_4, z_4)$ to a given set of another four points $P'_1(x'_1, y'_1, z'_1)$, $P'_2(x'_2, y'_2, z'_2)$, $P'_3(x'_3, y'_3, z'_3)$ and $P'_4(x'_4, y'_4, z'_4)$ a transformation matrix is used. Thus, if a matrix A is to be transformed to a matrix A', a transformation matrix T is used

A'=AT

The matrix multiplication gives

A≡[a$_{ij}$]

B≡[b$_{jk}$]

C=AB≡[a$_{ij}$]·[b$_{jk}$]≡[c$_{jk}$]  (19)

wherein $$c_{ik} = \sum_{j=1}^{n} a_{ij} b_{jk} \quad (20)$$

This is used for transforming points in the coordinate systems of the system according to the invention.

Figure 5:
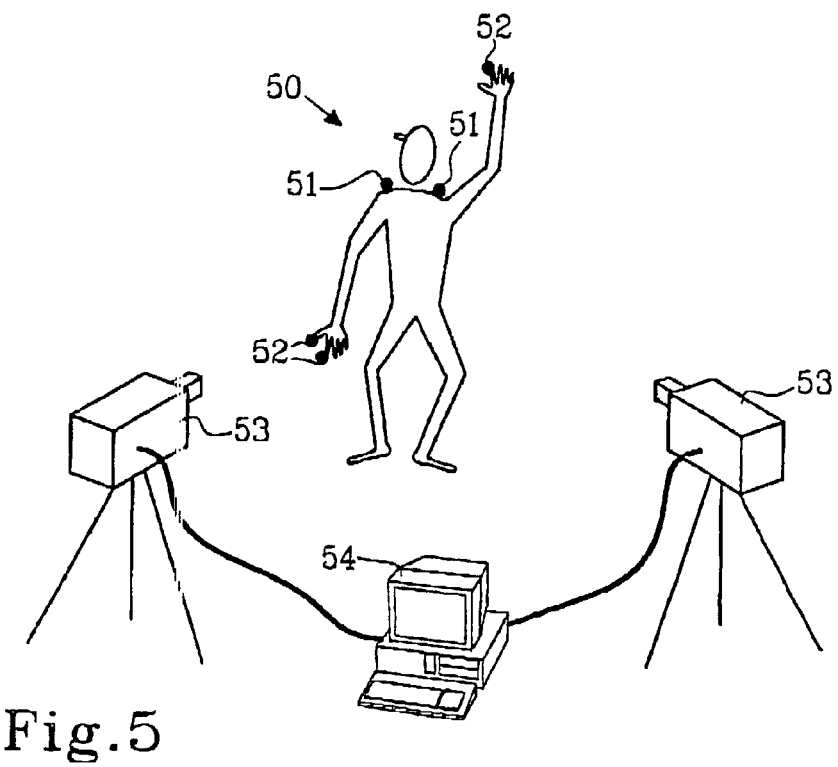
FIG. 5 is an example of an application using the system of the invention.

The system of the invention can be used for several applications. One application is illustrated in FIG. 5, in which the system is used as a virtual pointer device or mouse (VM). A user 50 is provided with a number of markers 51 and 52 (Alfa and Beta markers). A number of cameras 53 are arranged so that the user is within the field of view. The cameras are connected to a computer unit 54, which runs the system according to the invention. Thus, the movements (gestures) of the user are translated to commands, which affect the movements of, e.g. a pointer on the screen. This application is especially useful, for example when lecturing and using computers for showing images (overheads) etc., or controlling the computers. In this case, the system comprises additional functions for translating the gestures to pointer commands and adopting the movement of the markers (translating coordinates) to movements on the screen.

Figure 6:
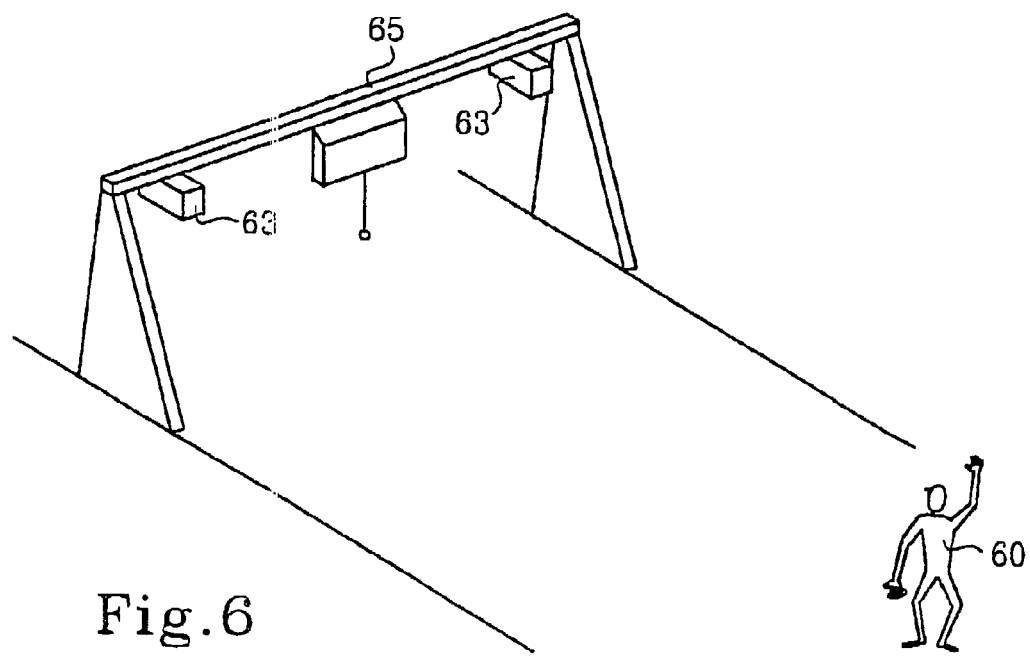
FIG. 6 is another exemplary application using the system of the invention.

Another application is illustrated in FIG. 6. In this case, the user 60 controls a crane 65. Cameras 63 are provided within the working area, preferably on the crane. The gestures of the user are then translated to commands for controlling the crane, such as moving forward/backwards, lifting etc. Other advantages of applying the invention in this case is that the objects in the way of the crane can be provided with markers so that the crane can avoid the marked places, or workers provided with markers, e.g. on their helmet, thus achieving a secure working environment.

Above-mentioned applications are, however, given merely as examples and do not limit the invention to such applications.

Figure 7:
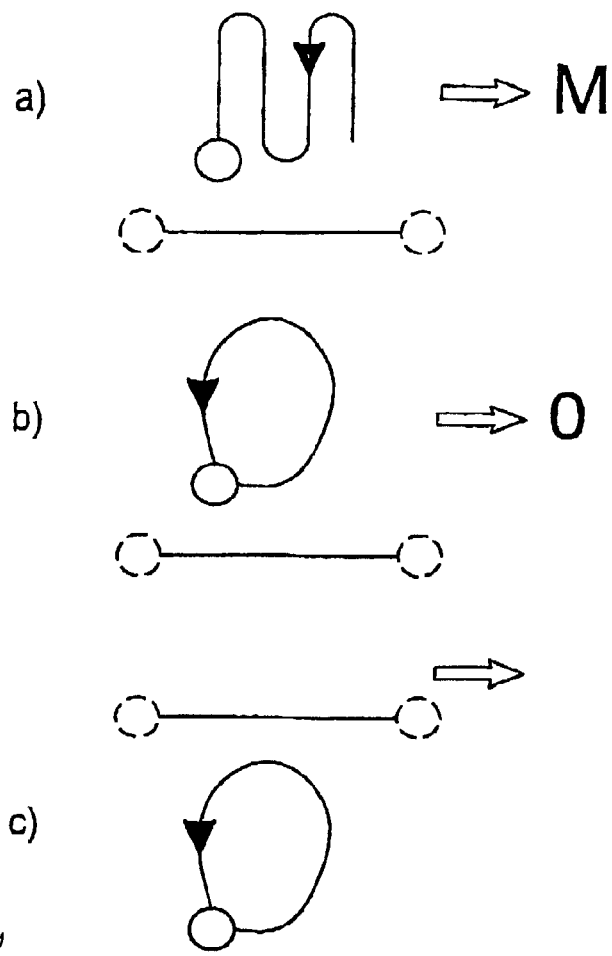
FIG. 7 illustrates schematic translation of the marker movements.

The function of the system is to detect the movements of a marker and relating the movement to a stored movement representation, which is translated to a command. To simplify the translation or to increase the command possibilities, the system uses alfa markers as a reference line and movements are translated or omitted with respect to the reference line, e.g. depending on the movement taking place above the line or beneath the line. FIG. 7 illustrates schematic translation of the marker movements. The left hand illustrates the translation results. In FIG. 7a the movement of marker 72 is above the reference line 76 comprising the distance between the alfa markers 71, and it is translated to an "M". Also, in FIG. 7b, the movement of marker 72 is above the reference line 76 and it is translated to an "O". In FIG. 7c the movement is under the reference line and it is omitted. The movements can also be translated to commands such as "Move", "Click" etc.

It is also possible to define some macro commands, i.e. a command that comprises of several commands and correspond to one gesture. In case of the crane application one gesture can mean to move to specific position and lift an object. The command sequence is recorded and related to the gesture.

It is also possible to use different hand gestures as different commands, e.g. using left hand movement for one command and right hand movement to another.

Moreover, the markers can also be arranged on other moving objects such as robots, etc.

In above examples optical markers and detection devices are exemplified. However, it is also possible to use radio or ultrasonic markers and detection devices.

The principle of the position detection in case of ultrasonic/radio is based on the registration of the time difference between the time when ultrasonic sound or radio signal is reaching checkpoints (microphones/transceivers).

Figure 8:
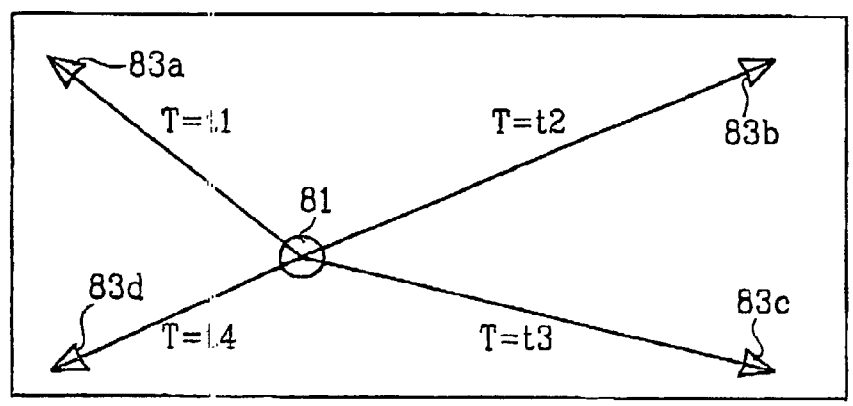
FIG. 8 shows the scheme of the position detection.

FIG. 8 shows the scheme of the position detection. The marker 81 in the centre of the room produce ultrasonic signal, which can be registered by four microphones 83a–83d (for 2D position detection is enough to have only two microphones, four can be used to determine better signal quality). Since the distance from marker to each of the microphones is different, they will register the signal in different moments of time.

The speed of sound wave propagation is above 330 m/s, which allows registration of that difference by devices based on the ordinary electronic components. If the variation in distance is 50 cm, the time difference will be approximately 0.5/330=0.00151 s.

The limitation of the accuracy of that system is:
The accuracy of the time measurement
The deviation of the speed of the sound propagation (may be caused by humidity, temperature)
Possible obstacles are:
Interference
Sound reflections
Ultrasonic emission of other electronic devices (such as computer monitors, floppy and hard disks, pulse power supplies, etc.)

In order to use many markers in one room with the possibility to detect each of them, it is suggested to use noise-like signal with the specific spectrum for each marker. This will allow also eliminate the disturbances caused by other sources of the ultrasonic emission.

Inertial sensor can detect the value of the acceleration of the object by each of three axes. That information can be used for determining the position of the object. The accuracy of the inertial sensors can be above 0.5%. The disadvantage of this method is that the analyzing unit will accumulate the detection mistake and require periodical calibration.

Taking into account the wide range of the requirements it seems logical to attempt create the system based on the low number of the module types, which combination will form the necessary configuration for the certain customer.

From the technological point of view the best solution is producing very few types of modules with adjustable characteristics.

Thus, the system of the invention can be used in a small room with the high requirements for the accuracy and lag time, but with low number of markers (for gesture recognition). Or, it can be used in the large rooms and corridors like in the hotel for guest or security guard position detection. That wide range of applications can be achieved by combination of several position detection methods and centralized processing of the position data.

Ultrasonic (radio) sensors can register presence of the marker in some certain room and its position there.

Inertial sensor can deliver information necessary to build a trajectory of the marker from the last calibration point, and therefore it's current position. Inertial markers are not associated with some certain room, only with the calibration points. For each marker it is necessary to evaluate and keep in memory the position, speed, direction, and acceleration. Even if ultrasonic sensors perform detection, that information will be required for inertial sensor calibration. Trajectory also can be stored, at least for the inertial sensors. Interesting feature may be the automatic testing of the inertial sensors. In case if marker situated in the room equipped by ultrasonic receivers, it is interesting to compare the difference in the position detection by both sensor types. It may be used for evaluation of the inaccuracy and calculation the necessary corrections for that certain inertial sensor.

Information delivered to the custom software can consist of
The room number and position in this room
The position of the last calibration and relative coordinates from this point There are two possible solutions for building ultrasonic system. One is using transponders in the markers and fixed microphones on the walls or ceiling. The second way is using microphones in the markers and fixed transponders mounted in the rooms.

Another side of the ultrasonic detection principle is the sequence of signal transmission. One approach is to fix time-of-fly of one signal to different points (sensors) in the room, and, the second is transmitting several signals, in order to measure each distance separately.

The example of the realization of the second way could look like the following:

There are several transponders, mounted on the walls. Each of them transmits specific signal in the specified order. Transmitted signal contains the time-code, and sensor code. Marker with the microphone receives the signals from each of the transponders, and, after decoding the time code, transponder's code, and comparing the fly time, it can determine its position.

The problem of that design is that for fast moving objects the position detection accuracy will be much lower, since signals will be received in different points.

In case of fixed microphones, ultrasonic (US) transponders in the marker, the US marker can consist of power supply, CPU (one-chip PIC) for signal generation and US transponder. There should also be some module, which will generate the command for US signal transferring. It is necessary because many markers are present, working simultaneously in the same room with the same receivers. It can be done by receiving command by radio channel, or by synchronizing the time counter of all markers.

Both ways have their specialty. Using the radio channel will limit the number of markers working simultaneously in the system, since the bandwidth of that (standard, 433 MHz) channel is only 40KBit/sek. The time synchronization will also have possible problems with clock deviation, and the attempt to eliminate this effect by increasing the gaps between the marker signals will also limit the number of markers, or the lag time.

Microphone units have microphone amplifier, signal decoding processor, and interface unit. Each microphone unit has internal clock synchronized with other microphone units. When microphone unit detects marker's signal, it sends to the central unit the marker ID and the registration time. Central unit based on the information received from the different microphone units evaluates the position of the marker and sends it to the Position server.

Marker is built of the command block, power supply, and US transponder. Using US transponders in the marker may be difficult due to high power consumption by these devices. However, marker in this case is very simple device, with almost no logic and low number of components inside. Simple working logic will decrease the cost of the software development, since the most of the logic can be programmed using the high level programming languages. The problem in this case is marker's synchronization and no possibility to use US detection principle together with the inertial method, because for the calibration of the inertial sensor it is necessary to have position information inside the marker.

In case if marker receives and decodes the US signal, microphone, amplifier and decoding module should be built into the marker. Marker in this case processes all information and can determine its position. Afterwards this information will be sent to the location detector. The advantage of that design is lower use of the radio channel and possibility to combine US and inertial sensors.

Inertial sensors can register the value of the acceleration and, therefore evaluate the relative coordinates from the starting point. In order to get more or less precise position information, the acceleration value should be measured quite frequently 1000 or more times per second. Due to requirement of many markers working simultaneously, measured values cannot be transferred to the location module with that speed, which means that this information should be processed inside the marker.

The information that markers send to the location module should in this case include Marker ID
The ID of the last calibration point
Relative position to the last calibration point The calibration point of the marker is the place where user receives marker from the administrator. In case if marker is equipped also by US module, It will calibrate the position each time user passes the US calibration point: doors, corridors, bar counter, etc. Calibration points should be placed taking into account the flow of the visitors/users. For example in the nightclub on the ferry, guests will frequently visit bar, toilet, pass doors. That makes possible to equip by USS calibration devices only that places, and follows marker movement on the rest of area by radio signals from inertial sensor.

For using markers as input devices for gesture recognition, there are some peculiarities considered.

The update rate of the marker position is much higher than for tracking. For gesture recognition more important is relative movement, not the exact position of the marker, which makes inertial markers more suitable for this purpose.

In case if the same hardware device is used as tracking system and as input device for the gesture recognition, there could be some special switch, which will allow the device to operate in different modes: gesture recognition and tracking. Switching to the gesture mode will increase the position update rate and will make possible the gesture recognition. Another way is to recognize simple gestures inside the marker and send to the position server the result of recognition also. That way will make possible using this device for tracking and control needs.

For example the guard checking the building rooms can use the marker for controlling the light, cameras, giving the (alarm) signals to other guards. Inertial markers can also be used for detection of dangerous situation, like if passenger falls out of the ferry, or if guard started to fight with some intruder. In all this cases there will be very special movements, which can be analyzed and corresponding actions can be preceded automatically.

Thus, the same modules as for optical detection can be used as for ultrasonic or radio markers. The same positioning, finding and coordinate translating methods as described above can be applied on the incoming signals.

The invention is not limited to the shown embodiments but can be varied in a number of ways without departing from the scope of the appended claims and the arrangement and the method can be implemented in various ways depending on application, functional units, needs and requirements etc. Thus, a combination of the detector devices (radio, sound, light) may also occur in same application.

The invention claimed is:

1. A gesture recognition system comprising:
a detecting arrangement for detecting a plurality of markers arranged on a movable object and generating signals corresponding to the markers;
a processing arrangement for processing said signals from said detecting arrangement;
a computing arrangement for determining positions of said markers from said signals;
a set of reference markers attached to the object and forming a reference line delimiting a first area and a second area;
a set of command markers attached to the object,
said detecting arrangement detecting movements of said command markers and translating said movements into gesture signals in said first area and omitting translation of said movements into gesture signals in said second area.

2. The system of claim 1, wherein said detecting arrangement is at least one camera and said markers are optically detectable markers.

3. The system of claim 1, wherein said detecting arrangement is microphones and said markers are ultrasound generating markers.

4. The system of claim 1, wherein said detecting arrangement is radio receivers and said markers are radio transponders.

5. The system according to claim 1, further comprising a memory for storing a gesture database in which a number of gesture types are stored and used for interpreting a gesture.

6. The system according to claim 1, further comprising a gesture recognition module, operatively arranged to receive an input stream of marker positions and compare a research gesture to template gestures and produce an estimation of similarity for every gesture in the database.

7. The system according to claim 1, wherein said gesture recognition is accomplished by analyzing for changes in direction and angles of said markers, said markers being divided into gesture fragments.

8. The system according to claim 1, wherein said gesture recognition is accomplished using coordinate transformations, wherein every gesture is entered in various places in space, under various angles and the gesture is transformed to a normal coordinate system.

9. The system according to claim 1, further comprising a noise filtering module for reducing noise in a marker data signal from said detection arrangement.

10. The system of claim 9, wherein said filter is a median filter, in which a filtered output for a marker at a time is taken from the middle of a stored array built from the position of markers before and after a given time.

11. The system according to claim 1, further comprising a gesture user interface driver, which interface driver serves as an emulation arrangement in an intermediate level between a control unit and a GUI module.

12. The system of claim 1, wherein said object is a human body and said set of reference markers is at least two markers attached to each shoulder of said human body.

13. The system of claim 1, wherein said first area is a space positioned above said references line and said second area is a space positioned below said reference line.

14. The system of claim 1, wherein said command markers comprises a physical property different from the reference markers, said physical property being detectable by said detecting arrangement for differentiating said command markers from said reference markers.

15. The system of claim 14, wherein said physical property is selected from a shape, a size, a color, a color combination and stripes.

16. The system of claim 14, wherein said physical property is a barcode.

17. A method of gesture recognition using a gesture recognition system, comprising:
detecting a plurality of markers arranged on a movable object and generating a signal corresponding to the markers;
processing said signals from said detecting arrangement;
determining positions of said markers from said signals;
computing a reference line from a set of detected reference markers delimiting a first area and a second area;

detecting movements of a set of command markers;

translating said detected movements of the set of command markers into gesture signals in said first area and omitting translation of said movements into gesture signals in said second area.

18. The method of claim 17, wherein said command markers comprise a physical property different from the reference markers, for differentiating said command markers from said reference markers.

19. A gesture recognition system, comprising:

a set of reference markers attached to a moving object and forming a moveable reference line delimiting a first area and a second area that move within space;

a set of command markers attached to the object; and a detecting arrangement i) detecting movements of the set of reference markers and computing a present position of the reference line delimiting a present location of the first area and of the second area, and ii) detecting movements of the set of command markers, the detecting arrangement translating the movements of the command markers detected within the present location of the first area into gesture signals and omitting translation of movements of the command markers into gesture signals for movements in the second area.

* * * * *